(12) United States Patent
Harel et al.

(10) Patent No.: US 9,072,311 B2
(45) Date of Patent: Jul. 7, 2015

(54) ABSORPTION OF FAT-SOLUBLE NUTRIENTS

(75) Inventors: Moti Harel, Baltimore, MD (US); John Piechocki, Odenton, MD (US); David J. Kyle, Catonsville, MD (US)

(73) Assignee: ADVANCED BIONUTRITION CORPORATION, Columbia, MD (US)

( * ) Notice: Subject to any disclaimer, the term of this patent is extended or adjusted under 35 U.S.C. 154(b) by 1344 days.

(21) Appl. No.: 10/530,598

(22) PCT Filed: Jun. 21, 2004

(86) PCT No.: PCT/US2004/019972
§ 371 (c)(1),
(2), (4) Date: Nov. 12, 2005

(87) PCT Pub. No.: WO2004/112767
PCT Pub. Date: Dec. 29, 2004

(65) Prior Publication Data
US 2006/0258623 A1 Nov. 16, 2006

Related U.S. Application Data

(60) Provisional application No. 60/479,507, filed on Jun. 19, 2003.

(51) Int. Cl.
| | | |
|---|---|---|
| A23K 1/18 | (2006.01) | |
| A23K 1/16 | (2006.01) | |
| A23K 1/00 | (2006.01) | |
| A23K 1/175 | (2006.01) | |
| A61K 31/065 | (2006.01) | |
| A61K 31/66 | (2006.01) | |

(52) U.S. Cl.
CPC ............... *A23K 1/1606* (2013.01); *A23K 1/004* (2013.01); *A23K 1/1603* (2013.01); *A23K 1/164* (2013.01); *A23K 1/1751* (2013.01); *A23K 1/1755* (2013.01); *A23K 1/1826* (2013.01); *A23K 1/188* (2013.01); *A61K 31/065* (2013.01); *A61K 31/66* (2013.01)

(58) Field of Classification Search
CPC ..... A23K 1/004; A23K 1/1606; A23K 1/164; A23K 1/188
See application file for complete search history.

(56) References Cited

U.S. PATENT DOCUMENTS

| | | | |
|---|---|---|---|
| 3,081,171 A | | 3/1963 | Reiners et al. |
| 5,364,563 A | | 11/1994 | Cathrein et al. |
| 5,897,866 A | * | 4/1999 | Bombardelli et al. ........ 424/777 |
| 5,935,808 A | | 8/1999 | Hirschberg et al. |
| 5,972,642 A | | 10/1999 | Fleno et al. |
| 6,022,701 A | | 2/2000 | Boussiba et al. |
| 6,036,992 A | * | 3/2000 | Borror et al. .................. 426/662 |
| 6,261,590 B1 | * | 7/2001 | Place et al. .................... 424/442 |
| 6,261,598 B1 | | 7/2001 | Runge et al. |
| 6,296,877 B1 | | 10/2001 | Auweter et al. |
| 6,358,524 B1 | | 3/2002 | Sedlacek et al. |
| 6,372,460 B1 | | 4/2002 | Gladue et al. |
| 6,403,056 B1 | | 6/2002 | Unger |
| 6,413,736 B1 | | 7/2002 | Jacobson et al. |
| 6,436,437 B1 | | 8/2002 | Yatvin et al. |
| 6,476,010 B2 | | 11/2002 | Koo et al. |
| 2002/0177181 A1 | | 11/2002 | Kanner et al. |

FOREIGN PATENT DOCUMENTS

| | | | |
|---|---|---|---|
| GB | 885677 | | 12/1961 |
| JP | 05124958 | | 5/1993 |
| JP | 06070698 A | * | 3/1994 |
| JP | 06269250 | | 9/1994 |
| WO | 94/14336 | | 7/1994 |
| WO | WO 9906585 A1 | * | 2/1999 |
| WO | 2004/082399 | | 9/2004 |
| WO | 2004/112776 | | 12/2004 |

OTHER PUBLICATIONS

Shao, Aquaculture pharmaceuticals and biolobicals: current perspectives and future possibilities, 2001, Advanced Drug Delivery Reviews, vol. 50, Issue 3, 229-243.*
Robles Medina et al., Downstream processing of algal polyunsaturated fatty acids, 1998, Biotechnology Advaces, vol. 16, Issue 3, 517-580.*
Bustos et al., Oxidatve stability of carotenoid pigments and polyunsaturated fatty acids in microparticulate diets containing krill oil for nutrition o marine fish larvae, Feb. 2003, Journal of Food Engineering, vol. 56, Issues 2-3, 289-293.*
Sargent et al., Lipid nutrition of marine fish during early development: current status and future directions, Aquaculture, vol. 179, Issues 1-4, Sep. 1, 1999, pp. 217-229.*
Clark et al., 2000, Lipids 35(7):803-6.
Hinostroza et al., 1997, Arch Lat-Amer. Nutr. 47(3):237-241.
Lockwood et al., 2003, J. Pharm. Sci. 92(4):922-926.
Pane et al., 1996, J. Biol. Res.—Boll Soc. It. Biol. Sper. 72(11-12):303-308.
Parajo et al., 1998, Biotechnol Bioeng. 59(4):501-506.
Shahidi et al., 1998, Crit. Rev. Food Sci. Nutri. 38(1):1-67.
Badmaev et al., 1999, Nutr. Res. 19:381-388.
Bell et al., 1998, J. Agric. Food Chem. 46(1):119-127.
Bjerkeng et al., 2000, Comp. Biochem. Physiol. B Biochem. Mol. Biol. 127(3):423-432.
Furuita et al., 1998, Aquaculture 161:269-279.
Goto et al., 2001, Biochim. Biophys. Acta 1512(2):251-258.
Shibata et al., 2001, Chem. Phys. Lipids 113(1-2):11-22.
Tsubokura et al., 1999, Int. J. Syst. Bacteriol. 49(Pt 1):277-282.

(Continued)

*Primary Examiner* — Gigi Huang
(74) *Attorney, Agent, or Firm* — RATNERPRESTIA

(57) ABSTRACT

Carotenoids are provided as dietary supplements to animal feed. These supplements improve the bioavailability of carotenoids by providing them in combination with phospholipids. The invention provides animal feeds for aquatic and terrestrial animals, and methods for making the feeds.

10 Claims, 1 Drawing Sheet

(56) References Cited

OTHER PUBLICATIONS

Yeum et al., 2002, Annu. Rev. Nutr. 22:483-504.
(Abstract Only) R.O. Canizares-Villanueva et al.; Microbial Pigments Sources; Rev. Lat. Amer. Microbiol.; 1998; 40; pp. 87-107, Abstract only.

Anonymous "Aquagrow DHA" Aug. 2, 2002) Retrieved from the internet: URL:http://web.achrchive. org/web/20020802172807/advanced bionutrition.com/html/prod_dha.htm.

* cited by examiner

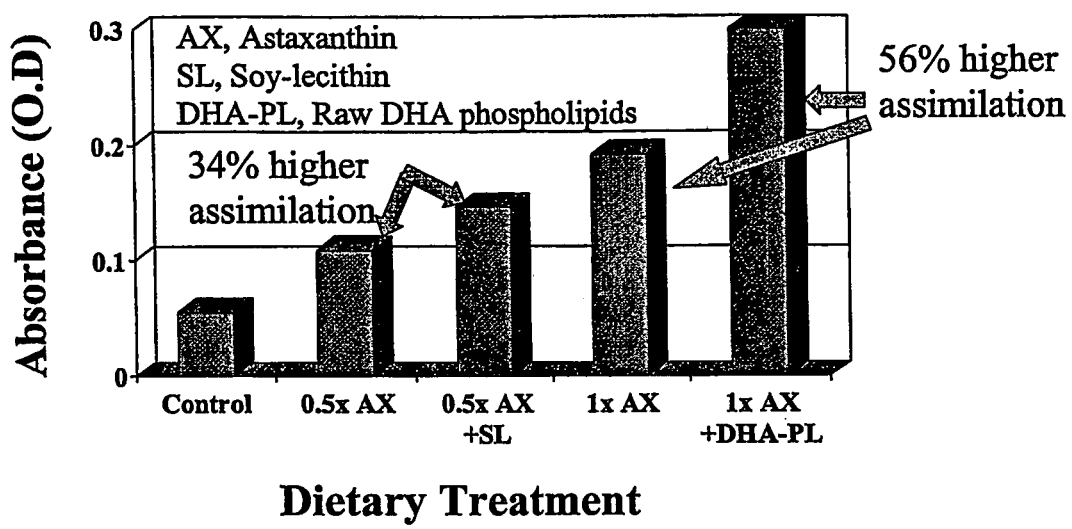

ABSORPTION OF FAT-SOLUBLE NUTRIENTS

BACKGROUND OF THE INVENTION

This application is related to improving the bioavailability of carotenoids as provided in formulated mixtures to animals. The invention provides both a specific composition and a method of manufacture for improved delivery of carotenoids.

This invention relates to a carotenoid composition and methods for its manufacture and use. In one aspect, the invention relates to carotenoids, synthetic or naturally produced by a single-celled organism, and phospholipids containing highly unsaturated fatty acids. In another aspect, the invention relates to methods of increasing carotenoid stability during feed processing and improving bioavailability in the gastrointestinal (GI) tract of coldwater species. In yet another aspect, the invention relates to using products made from these carotenoid compositions as a dietary supplement in various animal feeds.

The carotenoids, as a class of compounds, are classified into two main groups: carotenes and xanthophylls. In contrast to carotenes, which are pure polyene hydrocarbons, such as beta-carotene or lycopene, xanthophylls contain oxygen functional groups, such as hydroxyls, epoxy and/or oxo groups. Typical representatives of the xanthophyll group are astaxanthin, canthaxanthin and zeaxanthin.

A distinct red color is of prime importance to customer acceptance of a subset of food products, particularly aquatic food animals such as salmon, trout, shrimp, lobster and many other marine animals (Hinostroza, Huberman et al. 1997; Bjerkeng and Berge 2000). The oxygenated carotenoids (xanthophylls) are responsible for the red color of these aquatic animals. These xanthophylls are also useful for adding pigmentation to the flesh and products of other animals, and to other foodstuffs, for example poultry and eggs, various dairy products, snack foods, and the like.

Astaxanthin is the most abundant carotenoid present in the aquatic world (Shahidi, Metusalach et al. 1998). Aquatic animals, like terrestrial animals, generally cannot synthesize astaxanthin or any other carotenoid, although many of these animals accumulate carotenoid compounds that are present in their diets. Some of these animals, such as crustaceans, can interconvert some carotenes to xanthophylls, of which astaxanthin is the predominant compound formed. However, aquatic fish accumulate dietary astaxanthin even though these fish cannot convert any other carotenoid compound to astaxanthin. Therefore, the astaxanthin present in aquatic fish, and in products produced from these fish, must be derived directly from dietary sources.

Currently, synthetic astaxanthin is added to feeds of aquacultured salmonids to provide a source of this carotenoid (Bell, McEvoy et al. 1998). In some cases, synthetic canthaxanthin (another xanthophyll that is very closely related to astaxanthin) is used in place of astaxanthin in feeds for salmonids, but this compound does not function as well in these fishes as the naturally predominant astaxanthin (Bell, McEvoy et al. 1998).

Natural sources of dietary astaxanthin, including krill, crawfish, crustacean processing by-products, bacteria, yeast, algae, and higher plants are in great demand by aquacultural industries. However, these natural sources tend to be too expensive and of limited availability and reliability to be commercially viable. Lycopene is an alternative natural carotenoid that might meet the cost criterion for inclusion in feeds (Clark, Yao et al. 2000). It is in a class of carotenoids that characteristically gives color to many vegetables.

Carotenoids are easily isomerized by heat, acid or light. Once isomerized, they lose their biological antioxidant properties (Fennema 1996). The high demands placed on xanthophyll-containing formulations with respect to coloring action and bioavailability can thus not always be met because of these problems (Yeum and Russell 2002). Indeed, various processes and a number of combined emulsifying/spray-drying processes (see patents DE-A-12 11 911 or in EP-A-0 410 236) have been proposed to improve the color yields and to increase the absorbability or bioavailability carotenoids.

One specific problem which has not yet been addressed is related to the low body temperature of salmonid fishes, which is equal to the temperature of the water in which they inhabit, generally 0 to 14° C. Natural astaxanthin, especially those in *Phaffia* yeasts, are concentrated in oil droplets that contain about 13% palmitic acid (16:0) with a melting point of 64° C., and about 32% oleic acid (18:1n9) with a melting point of 16° C. (Deuel 1951). Because of these high melting point fatty acids, the astaxanthin containing oil droplets solidify near 10° C. This makes it difficult for the fish to incorporate the astaxanthin from the solidified oil droplet at water temperatures below 10° C. This is especially problematic for coldwater fish.

BRIEF SUMMARY OF THE INVENTION

The invention alleviates these problems by providing a process for preparing a mixture of carotenoids and phospholipids rich in highly unsaturated fatty acids (PUFA). The process comprises the following steps:

a) Preparing a molecularly-associated composition of carotenoids and a phospholipid with an edible oil or a mixture of water and a water-miscible organic solvent. If appropriate, a water-dispersible dry powder could also be prepared. To achieve dispersion, e.g., in the form of a suspension or an emulsion, it is advantageous to use an edible oil (such as, but not limited to, sesame oil, corn oil, cottonseed oil, soybean oil, or peanut oil) plus esters of medium chain-lengths vegetable fatty acids or fish oils (such as, but not limited to, mackerel, capelin, menhaden or cod liver oil).

b) Further increasing the stability of the carotenoids to oxidative decay by adding stabilizers such as, but not limited to, alpha-tocopherol, t-butylated hydroxytoluene, t-butylated hydroxyanisole, ascorbic acid or ethoxyquin.

c) Providing the carotenoids used to produce the composition from natural sources and/or synthetic sources.

d) The phospholipids used to produce the composition are rich in polyunsaturated fatty acids (PUFA) having two or more double bonds in at least 20% of total fatty acids.

e) The carotenoid composition according to the invention can also contain at least one other active substance in concentrations of 0.01 to 40% by weight.

Possible examples of these active substances are the following:

Other carotenoids such as for example bixin, zeaxanthin, cryptoxanthin, citranaxantin, canthaxanthin, astaxanthin, beta-apo-4-carotenal, beta-apo-8-carotenal, beta-apo-8-carotenoic esters, lycopene, or lutein, singly or as a mixture.

Vitamins, such as vitamin A, vitamin A acetate, vitamin A palmitate, riboflavin, vitamin $B_{12}$, ascorbic acid, ascorbyl palmitate, nicotinic acid, nicotinamide, pyridoxine hydrochloride, vitamin $D_3$, tocopherol, tocopherol acetate, tocopherol palmitate, tocotrienol, vitamin K, thiamine, calcium pantothenate, biotin, lipoic acid, folic acid, and folic acid derivatives (such as tetraBASF hydrofolic acid, 5-methyltetrahydrofolic acid, 10-formyltetrahydrofolic acid) and 5-formyltetrahydrofolic acid).

Compounds with vitamin or coenzyme characteristics, such as choline chloride, carnitine, taurine, creatine, ubiquinones, S-methylmethionine, and S-adenosylmethionine.

Polyunsaturated fatty acids, such as linoleic acid, linolenic acid, arachidonic acid (ARA), eicosapentaenoic acid (EPA), and docosahexaenoic acid (DHA) and esters thereof including but not limited to triglycerides.

Glutathione and its esters such as, for example GSH monomethyl ester, GSH dimethyl ester, GSH monoethyl ester, and GSH diethyl ester.

Depending on the nature of the formulation, it may contain, besides the carotenoids, at least one other additive such as, for example, oils, protective colloids, alkaloids (such as peperine (Badmaev, Majeed et al. 1999)), and antioxidants.

Examples of protective colloids that can be used are gelatin, fish gelatin, starch, dextrin, plant proteins, pectin, gum arabic, casein, caseinate, or mixtures thereof. It is also possible to employ polyvinyl alcohol, polyvinylpyrrolidone, methylcellulose, carboxymethylcellulose, hydroxypropylcellulose, and alginates.

To increase the mechanical stability of the dry powder, it is also possible to add to the colloid a plasticizer such as sugars or sugar alcohols, such as sucrose, glucose, lactose, invert sugar, sorbitol, mannitol, or glycerol.

The use of the PUFA-rich phospholipids as part of this formulation also provides additional benefit to the survival and health of the animal consuming the invention's formulation (Bracco and Deceekbaum 1992; Furuita, Takeuchi et al. 1998; Place and Harel 2002).

The present invention provides a mixture comprising a carotenoid and PUFA-rich phospholipid.

The present invention provides a composition comprising a mixture including a carotenoid either in synthetic or natural form and a phospholipid having at least 20% PUFA, where the phospholipid is in an amount sufficient to improve carotenoid stability and bioavailability and prevent solidification when the composition is fed to coldwater species, and the carotenoid is in an amount sufficient to produce acceptable coloring in edible tissues.

The present invention also provides a molecularly-associated complex comprising a carotenoids and a phospholipid.

The present invention provides a composition comprising a molecularly-associated complex including an amount of a carotenoid and an amount of a phospholipid, wherein the amount of the phospholipid is sufficient to improve carotenoids stability and bioavailability and prevent solidification when the composition is fed to coldwater species and the amount of the carotenoid is sufficient to produce acceptable coloring of edible tissues.

The present invention also provides a mixture comprising a carotenoid, a phospholipid, and a bioactive compound, or a bioactive complex (comprising a carotenoid/phospholipid/bioactive compound), and/or mixtures or combinations thereof.

The present invention provides a composition comprising a mixture including a carotenoid, a phospholipid and a bioactive compound, a bioactive complex, or mixtures or combinations thereof, wherein the phospholipid is present in an amount sufficient to improve the carotenoids' stability and bioavailability and prevent solidification when the composition is fed to coldwater species, and wherein the amount of the total carotenoid is sufficient to produce acceptable coloring of edible tissues.

The present invention provides a composition comprising a cellular material and a phospholipids wherein the phospholipid to cellular material is in the ratio of from about 1:1 to about 1:100 and the cellular material comprises long chain polyunsaturated fatty acids and/or carotenoids.

The present invention also provides a method for making a carotenoid-containing composition with increased carotenoid stability and bioavailability with low melting temperature when fed to cold-water species, including the step of mixing carotenoids and a PUFA-rich phospholipid. The method can further include the step of mixing the carotenoid/phospholipid composition with another bioactive compound forming an alternative and useful composition.

The present invention also provides a method for making a carotenoid-containing composition with increased stability and bioavailability including the step of contacting a carotenoid and a phospholipid under conditions sufficient to maintain the carotenoid and the phospholipid in a molecularly-associated form. The method can further include the step of admixing the carotenoid/phospholipid molecular association with a bioactive compound.

The present invention also provides for making a long chain polyunsaturated fatty acid (LC-PUFA) composition with increased stability and bioavailability including the step of contacting a cellular material containing said LC-PUFA and a phospholipid under conditions sufficient to maintain the LC-PUFA and the phospholipid in a molecular association form. The method can further include the step of admixing the LC-PUFA/phospholipid molecular association with a bioactive compound.

The present invention also provides a method for enhancing the pigmentation of coldwater animals by providing such animals with a feed enriched with a composition that consists of a cellular source of carotenoid such as, but not limited to *Phaffia* yeast, *Haematococcus* algae, marigold flowers, mixed with a PUFA-enriched phospholipid such as, but not limited to, plant lecithins, egg yolk lecithin, phospholipid-rich extracts from animals or animal byproducts, and phospholipid-rich extracts from microbial sources. The cellular or synthetic carotenoid material and phospholipid material are premixed and homogenized prior to the addition to a feed in order to stabilize and solubilize the carotenoid and such a process surprisingly results in the enhanced bioavailability of the carotenoids by the coldwater animal.

BRIEF SUMMARY OF THE SEVERAL VIEWS OF THE DRAWINGS

FIG. 1. Improved total carotenoid content of rainbow trout using conditions as described in Example 5 (for the Astaxanthin compared to Astaxanthin+DHA-phospholipid) and Example 4 for Astaxanthin compared to Astaxanthin+soy lecithin. The control had no added astaxanthin in the diet (some residual carotenoids were in the original diet). The soy lecithin gave a 34% higher incorporation of astaxanthin (AX) than AX alone. The DHA-rich phospholipid gave 56% higher incorporation of AX than AX alone.

DETAILED DESCRIPTION OF THE INVENTION

Definitions

Unless otherwise stated, the following terms shall have the following meanings:

The term "solution" means a liquid and any mixture of a liquid and a solid that has fluid attributes, e.g., flowable or having appreciable fluidity at standard temperature and pressure, including, without limitation, a dispersion of a solid(s) in a liquid, an emulsion, a slurry, a micro-emulsion, colloidal suspension, a suspension, or the like.

An "emulsion" is suspension of one liquid in another with which the first will not mix. The first liquid can be suspended as small globules in the second liquid. An oil or an aqueous form of the compositions of this invention can be emulsified into an aqueous solution.

An "active substance" is any material that functions or is capable of functioning in a manner characteristic of that substance.

The term "molecular association" or "molecularly-associated" means a combination of two or more molecular species associated via any known stabilizing atomic or molecular level interaction or any combination thereof, where the interactions include, without limitation, bonding interactions such as covalent bonding, ionic bonding, hydrogen bonding, coordinate bonding, or any other molecular bonding interaction, electrostatic interactions, a polar or hydrophobic interactions, or any other classical or quantum mechanical stabilizing atomic or molecular interaction.

The term "species" is defined as any species in the animal kingdom, including mammals, fish, crustaceans and mollusks.

An "aquatic animal" is an animal that lives primarily in an aquatic environment, and includes fish, crustaceans, and mollusks. Aquaculture methods and/or commercial production practices have been developed to cultivate aquatic animals.

A "fish" and the plural "fish" are defined in this invention as any Ostiechthyean or Chondrichthyean fish, such as, but not limited to, sharks, rays, sturgeon, eels, anchovy, herring, carp, smelt, salmon, trout, hakes, cod, rockfish, bass, drum, mackerel, tuna, butterfish, catfish, flounder, and seabream.

A "crustacean" and the plural "crustaceans" are defined in this invention as any member of the Class Crustacea, such as, but not limited to, shrimp, lobsters, red claws, and crabs.

A "terrestrial animal" is one that lives primarily on land in a non-aquatic environment, such as, but not limited to cows, pigs, and chickens.

The term "phospholipid" refers to any lipid or fatty acid having a covalently attached a phosphate group in the molecular structure. These phospholipids are preferably sourced from vegetable material such as, but not limited to, soy, corn, palm, canola, rice, flax, coconut, combinations thereof, and are usually obtained as byproduct of the process of refining the vegetable oil. These phospholipids may be comprised of any of phosphatidyl choline (PC), phosphatidyl serine (PS), phosphatidyl ethanolamine (PE) and/or phosphatidyl inositol (PI), or a combination thereof.

The term "PUFA-rich phospholipid" means a phospholipid containing at least 20% fatty acids with 2 or more double bonds.

The term "carotenoid" encompasses any molecule in a class of yellow to red pigments, including carotenes and xanthophylls. "Carotenes" are orange-yellow to red pigments that are found in some animal tissues and plants, and may be converted to Vitamin A in the liver. "Xanthophylls" are yellow pigments, some of which may be found with chlorophyll in green plants.

Description

The inventors have found that a unique mix, including carotenoid compounds and PUFA-rich phospholipid (such as soy lecithin, DHA-, EPA- or ARA-rich phospholipid extracts) improves the bioavailability of carotenoids when consumed by coldwater fish. Additionally, the phospholipids increase oxidation stability of the carotenoids compared to other types of standard preparations. It is well documented that carotenoids are sensitive to photo- and thermal-oxidation, which results in major carotenoid losses during feed preparation and storage. Moreover, natural sources of carotenoids include a high level of saturated oils. Saturated oils become solidified at low water temperature and thereby reduce bioavailability of the carotenoid in the animal GI tract. The present invention overcomes the problems associated with standard carotenoid formulations by combining carotenoids with PUFA-rich phospholipid, where the phospholipid increases the efficacy of the carotenoid absorption at low temperatures.

The present invention relates broadly to formulations including carotenoids and PUFA-rich phospholipid compositions. Additionally, methods for producing such compositions and their use in formulation of novel feeds are disclosed.

Examples of phospholipid include, without limitation, phosphatidyl cholines (such as phosphatidyl choline (PC), dipalmitoylphosphatidylcholine (DPPC), other disaturated phosphatidyl cholines), phosphatidyl ethanolamines, phosphatidylinositol, phosphatidyl serines (sphingomyelin or other ceramides), various other phospholipids, phospholipid-containing oils (such as lecithin oils derived from soy beans), or mixtures and combinations thereof The phospholipids of the present formulation can also be found in PUFA-rich extracts of single cell organisms such as, but not limited to, *Crypthecodinium* sp., *Schizochytrium* sp., *Mortierella* sp. and *Paracoccus* sp. Phospholipids of the present invention can also be derived from animal sources including, but not limited to, animal organ extracts (e.g., brain, liver, other animal process wastes), egg yolk, egg yolk extracts, fish byproducts and fish byproduct extracts (i.e., processed waste products from preparation of fish meal or purified fish oil). Preferred phospholipids are from *Crypthecodinium* sp., *Schizochytrium* sp. and *Mortierella* sp., and plant lecithins. Phospholipids useful for this invention would be those wherein at least 20% of the fatty acid residues have 2 or more double bonds. Preferred phospholipids would be those containing at least 20% of the fatty acid residues with 3 or more double bonds. Particularly preferred phospholipids would be those containing at least 10% of the fatty acid residues with 4 or more double bonds. Most particularly preferred phospholipids would be those containing at least 20% of the fatty acid residues with 4 or more double bonds.

Generally, the weight ratio of carotenoids to PUFA-rich phospholipid is between about 2:1 and about 1:100, with ratios between about 2:1 and 1:50 being preferred and ratios between about 1:1 and 1:10 being particularly preferred and ratios between about 1:1 and about 1:5 being especially particularly preferred.

The effective amount of the carotenoids for use in the composition of this invention ranges from about 0.1 mg per kg feed to about 1000 mg per kg feed depending on the carotenoids and the phospholipid used in the composition. Amounts between about 1 mg per kg feed to about 500 mg per feed being preferred, with amounts between about 2 mg per kg feed and 50 mg per feed being particularly preferred. A sufficient amount of phospholipid is generally an amount of phospholipid between about 0.01 mg per mg carotenoids and about 5000 mg per mg carotenoids, with amounts between about 0.5 mg per mg carotenoids and 2500 mg per mg carotenoids being preferred, and amounts between 2 mg per mg carotenoids and about 250 mg per mg carotenoids being particularly preferred, and amounts between about 2 mg per mg carotenoids and about 100 mg per mg carotenoids being especially particularly preferred.

The compositions of the present invention can be in any desirable form, including, without limitation, a solid (such as a powder, granules, a semi-solid such as a paste or the like), an emulsion, or a solution. An emulsion means that an oil or aqueous form of the compositions of this invention is emulsified in an aqueous solution. In addition, the emulsion can be a standard emulsion or a micro-emulsion where the mixture is forced through a nozzle or in other methods that generate micro-emulsions. Solutions of this invention employ a suitable solvent in which the composition is soluble or highly soluble.

Generally, the compositions of this invention are formulated to be directly mixed with other feed ingredients prior to processing. However, the formulations can also be emulsified or blended with a carrier oil to top-coat the feed after processing.

In formulations of this invention that combine a phospholipid, such as lecithin, and a carotenoid, such as astaxanthin, the phospholipid acts to prevent oxidation of the carotenoids as well as to improve its solubility. Thus, the formulations of this invention, which supplement carotenoids with phospholipids, show significantly more stability, thus removing a major impediment that severely limits the utility of natural carotenoids in feed preparation. The carotenoid/phospholipid formulations of this invention not only have increased stability, but the formulations also increase the bioavailability of the carotenoids when taken by coldwater animals. Current carotenoid formulations contain large quantities of high melting temperature oils. These preparations therefore lose a major part of their effectiveness when taken by coldwater species due to the phase of the oil (i.e., solid). The carotenoids of the invention associate with PUFA-rich phospholipids in such a way as to preserve their liquidity and become more available for uptake in the small intestines, especially at low temperatures. Additionally, it is thought that the PUFA-rich phospholipid-carotenoid formulations of this invention improve carotenoid bioavailability by interfering with the interaction of carotenoids with other feed components during digestion in the fish stomach, permitting carotenoids to exit the stomach in a bioavailable form.

For example, the carotenoids (naturally produced by a single celled-organism or synthetic) can be combined with different concentrations of either purified phospholipids or crude phospholipids. For example, PC is available in a purified form comprising>90% PC or in crude extracts from soybeans in de-oiled and oiled states (American Lecithin Company). Crude phospholipid extracts containing over 40% DHA or ARA of total fatty acids are also available (Advanced BioNutrition Corp., Columbia, Md.). The presence of PUFA-rich phospholipid, such as lecithin, in the formulations of this invention prevents carotenoid solidification, thereby increasing bioavailability of carotenoids in the GI tract of coldwater species. Thus, the presence of a PUFA-rich phospholipid in the compositions of this invention allows a reduction in carotenoid dosages in feed and the shortening of the administration period prior to harvesting without loosing the desired coloring.

Further improvement in bioavailability may be achieved by the addition of an alkaloid, such as piperine, to the carotenoid/phospholipid composition.

The addition of PUFA-rich phospholipids can also significantly increase the bioavailability of the carotenoids. This is an improvement, since in certain instances carotenoids have bioavailabilities of about 50% or less necessitating relatively large doses of the carotenoids for a longer period of time. The PUFA-rich phospholipids result in improved bioavailability of the carotenoids especially by coldwater species. The improved bioavailability can range from about a 20% increase to as much as about a 60% or greater increase by carefully choosing the type of PUFA-rich phospholipid and the ratio of the carotenoids and PUFA-rich phospholipids.

It should be noted that a number of substances that are used as additives to enhance carotenoid absorption are known irritants or damaging agents of the GI mucosa. Therefore, these would be contraindicated for use with carotenoids. Such substances would include: short chain fatty acids (such as citric acid, decanoic acid, caprylic acid or the like), long-chain unsaturated free fatty acids (such as oleic acid or the like), detergents (such as BRIJ, TWEEN-80, sodium deoxycholate, or the like), and chelators of polyvalent metal cations (such as EDTA, EGTA, or the like).

Because of their degree of unsaturation, carotenoids are inherently prone to oxidative degradation. Preserving the integrity of the double bonds of the carotenoids through processing and storage is a critical problem in the preparation of feeds, food and supplements therefore containing such materials. At the same time the preservation of the double bonds of the carotenoids is critical for the efficacy of the carotenoid itself. Kyle and Becker (WO 00/54575) have described a process whereby a DHA-containing oil is stabilized by lecithin at levels up to 8% of the oil. AN additional aspect of this invention involves the combination of lecithin with the carotenoid containing material is in the stabilization of the carotenoid against oxidation.

Another aspect of the present invention is the combination of the lecithin with other cellular materials comprising long chain polyunsaturated fatty acids (LC-PUFAs). Microorganisms such as, but not limited to, *Crypthecodinium, Schizochytrium, Theraustochytrium, Ulkenia, Mortierella*, etc. are prone to oxidation as a result of their high content of LC-PUFA. *Schzochytrium, Thraustochytrium* and *Ulkenia*, in particular, are very fragile and can release oil during the process of harvesting and drying. The use of high concentration of phospholipids (especially lecithin) during the drying process can impart a high degree of stability to the resulting dry biomass of these microorganisms and increase the bioavailability of the LC-PUFAs themselves. Lecithin to biomass ratios from about 1:100 to about 1:1 are effective in increasing stability and bioavailability of the oils.

Methods for Making Carotenoid/Phospholipid Compositions

One preferred class of compositions of this invention are compositions that include a carotenoid or carotenoids and PUFA-rich phospholipid or PUFA-rich phospholipids generally prepared by contacting carotenoid and phospholipid under conditions to promote molecular association of the carotenoid and phospholipid. Such conditions typically will include the use of mixing procedures that promote molecular interactions and associations, use of a solvent and/or buffer, and controlled physical parameters (such as temperature, pressure and time) to permit an optimal degree of interaction and association.

The chemical interaction is preferably performed by aggressive or vigorous mixing. Such mixing procedures include vortex mixing, other high shear mixing procedures, sonication, other molecular level mixing procedures, or the like. The time and temperature of mixing should be designed to maximize interactions between the carotenoids and the phospholipids without causing thermal or shear damage to the molecules themselves. Generally, the mixing time will range from about 5 minutes to several hours, with times ranging between 10 minutes and 1 hour being preferred.

Generally, the mixing temperature will range from ambient to a temperature of at least 10% below the lowest breakdown temperature for the carotenoids or phospholipids being mixed. Preferably, the temperature will be between ambient temperature to about 60° C.

In preparing the formulations of this invention, the carotenoids can be mixed with synthetic, purified naturally derived, or crude phospholipids or can be mixed with various grades of lecithin or other PUFA-rich oils obtained from single-celled organisms. Carotenoids may be in the form of pure carotenoid (synthetic or otherwise) or as cellular material from high carotenoid microorganisms such as but not limited to *Pfaffia* or *Heamatococcus* and the mixture of phospholipids to microbial cell biomass may be in the range from 1 part phospholipid to from 1 to 100 parts cellular biomass. Especially useful phospholipid concentrations range from about 15 to about 93% PC by weight. Moreover, the formulations can use either de-oiled or oil-based phospholipid preparations.

Regardless of the form of the phospholipid, generally the ratio of carotenoids to phospholipids ranges from about 1:100 to about 10:1, preferably, from about 1:25 to about 2:1, and particularly from about 1.0:10.0 to about 1.0:1.0.

In formulations using de-oiled phospholipids, the de-oiled phospholipids are initially dissolved in an organic solvent such as ethanol, and then mixed with carotenoids. This is followed by mixing, such as vortexing and/or sonication mixing. In formulations using oiled phospholipids, the oil-based phospholipids are simply combined with a carotenoid compound and mixed by vortexing and/or sonication, if needed. Sonication or mixing temperatures are preferably between ambient and about 60° C.

Another preferred process for making the compositions of this invention includes the dissolving of phospholipids and carotenoids in a polar solvent. Suitable solvents include, without limitation, chlorocarbons (such as chloroform, or the like), lower alcohols (such as methanol, ethanol, isopropanol or the like), or any other solvent in which the phospholipids and the carotenoids have some solubility, and the solvent is removable, e.g., by evaporation, or the like.

Methods for making LC-PUFA phospholipids compositions. In preparing the formulations of this invention, the LC-PUFA-containing biomass such as, but not limited to *Schyzochytrium*, can be mixed with synthetic, purified naturally derived or crude phospholipids or can be mixed with various grades of lecithin or other PUFA-rich oils obtained from single cell organisms. Especially useful phospholipids concentrations ranging from about 15 to about 93% PC by weight. Moreover, the formulations can use either de-oiled and oiled-based phospholipids preparations. Mixtures of phospholipids and cellular material containing LC-PUFAs can range from 1 part to from 1 to 100 parts cellular material.

EXAMPLES

The following examples are included for example only to illustrate the preparation of compositions of present invention containing a carotenoids and PUFA-rich phospholipid, and are in no way meant to limit the scope or teaching of this invention.

Example 1

Preparation of a Composition of Synthetic Astaxanthin and Soy Lecithin.

A sample of 60 g of soy lecithin (American Lecithin Co) was dissolved in ethanol, 30 g synthetic astaxanthin (AHD International, Atlanta, Ga.) was added, the mixture sonicated at 60° C. for 5 minutes, and the solvent evaporated under vacuum. The resulting powder can be incorporated with other feed ingredients or dissolved in oil and top-coated onto the feed particles.

Example 2

Preparation of a Composition of *Haematococcus* (Containing Natural Astaxanthin) and Phospholipid Extract from *Crypthecodinium* Species.

A sample of 50 g of algal phospholipids (Advanced Bio-Nutrition, Columbia, Md.) and 100 g *Haematococcus* (Naturose, Cyanotech Corporation Kailua-Kona, Hi.) were mixed vigorously for 1 h at room temperature. The mixture was dissolved in 850 ml of Menhaden oil (Omega Protein, Houston, Tex.) and used to top-coat standard fish feed pellets. The feed pellets were top coated at a level of 20 g of the above mixture per kg feed. This produced a feed containing about 50 mg astaxanthin per kg feed. This feed was then used to color the flesh of aquatic animals that consumed the feed.

Example 3

Preparation of a Composition of *Phaffia rhodozyma* Yeast Biomass and Phospholipid Extract from *Crypthecodinium* sp.

*Phaffia* yeast was grown under standard conditions in a fermentor and biomass was harvested by centrifugation and diluted to 30% solids with water. Then 13.3 g of algal phospholipids (8 g on a dry weight basis) (ABN, Columbia, Md.) was mixed vigorously with 333 g of the *Phaffia* slurry (100 g on a dry weight basis) to facilitate molecular association between the carotenoid and the phospholipids. The material was then dried on a rotary drum dryer at low temperatures and the resulting flakes were milled under liquid nitrogen to produce a coarse powder. The resulting powder was then mixed with a commercial trout feed and cold pressed into feed pellets (1.2-2.0 mm, Ziegler Bros Inc. Gardners, Pa.) using standard techniques.

Example 4

Preparation of a Composition of *Phaffia rhodozyma* Yeast Biomass and Soy Lecithin.

One hundred grams of *Phaffia* yeast biomass (Archer-Daniels-Midland Company, Decatur, Ill.) was mixed with water to give a slurry with a 30% water content. Eight g of soy lecithin (American Lecithin Co) was added to the slurry and the resultant mixture was homogenized vigorously to facilitate molecular association between the carotenoid and the phospholipids. The slurry was then dried in a freeze dryer and collected as a powder. This material had the following composition: 1.5% astaxanthin, 8% phospholipid, 50% fatty acids with 2 or more double bonds, and 20% of the fatty acids with 4 or more double bonds. This mixture was then incorporated into 10 kg commercial fishmeal pellets using standard methods with cold pressing or cold extrusion (Ziegler Bros Inc. Gardners, Pa.).

Example 5

Feeding of Trout Fish with a Feed Containing Natural Astaxanthin from *Phaffia* and a PUFA-Containing Phospholipid.

Five diets were prepared by Ziegler Bros Inc. (Gardners, Pa.) according to the following compositions:

Diet 1 contained 12.5 g *Phaffia* biomass per kg feed (100 mg astaxanthin/kg feed).

Diet 2 contained 13.8 g of the composition described in Example 3 per kg feed (100 mg astaxanthin/kg feed).

Diet 3 contained 7.6 g of the composition described in Example 3 per kg feed (50 mg astaxanthin/kg feed).

Diet 4 contained no *Phaffia* (0 mg astaxanthin/kg feed).

Diet 5 contained 7.6 g of the composition described in Example 4 per kg feed (50 mg astaxanthin/kg feed).

Five groups of 20 trout fish per group were fed 4.4% body weight/day for 21 days. White muscle tissues were sampled from 5 fish in each group on day 21 and freeze-dried for 48 h.

Total carotenoids were extracted from the tissues by homogenizing in 5 ml of absolute ethanol and 5 ml ethyl acetate. The homogenates were centrifuged (1000×g for 5 min) and the supernatants dried under a stream of nitrogen and dissolved in 2 ml of hexane. Total carotenoids were measured spectrophotometrically at 470 nm.

The effect of the diet on muscle pigmentation is presented in Table 1:

TABLE 1

|  | Absorbance at 470 nm |
|---|---|
| Diet 1 | 0.19 |
| Diet 2 | 0.30 |
| Diet 3 | 0.11 |
| Diet 4 | 0.05 |
| Diet 5 | 0.14 |

As can be seen from Table 1, Diet 4, with no *Phaffia* and no astaxanthin, provided the least amount of muscle pigmentation indicative of carotenoid content ($A_{470}$=0.05). Diet 3 and Diet 5, with no *Phaffia* and 50 mg astaxanthin provided by the compositions of Example 3 and Example 4, respectively, provided intermediate amounts of muscle pigmentation. Diet 1, with *Phaffia* biomass providing twice as much, i.e., 100 mg astaxanthin, provided only a slightly higher amount of coloration than Diets 3 and 5. Diet 2, with no *Phaffia* and 100 mg astaxanthin provided by the composition of Example 3, provided the highest amount of coloration. It improved the muscle coloring by 56%, compared to Diet 1.

Example 6

Preparation of *Schyzochytrium* Biomass with a High Degree of Oxidative Stability.

*Schizochytrium* biomass is produced using conventional fermentation technology and harvested by centrifugal harvesting processes to a solid content of about 20%. To this 100 g of slurry (20 g dry weight *Schizochytrium* containing about 10 g of LC-PUFA enriched oil) 2 g of soy lecithin (American Lecithin Co.) is added. The resultant mixture is thoroughly mixed and then dried using a rotary drum dryer, or any other drying process and collected as powder of flake. The resulting flake product has a high degree of oxidative stability and bioavailability relative to a similar product produced without the lecithin treatment.

While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

All references cited herein are incorporated by reference, including the following.

Patent References
U.S. Pat. No. 6,261,598
U.S. Pat. No. 6,476,010
U.S. Pat. No. 6,436,437
U.S. Pat. No. 6,403,056
U.S. Pat. No. 6,358,524
U.S. Pat. No. 6,296,877
U.S. Pat. No. 6,413,736
U.S. Pat. No. 6,022,701
U.S. Pat. No. 5,972,642
U.S. Pat. No. 5,935,808
PA20020177181
EP-A-0 410 236
DE-A-12 11 911

Literature References

Badmaev, V., M. Majeed, et al. (1999). "Piperine, an alkaloid derived from black pepper increases serum response of beta-carotene during 14 days of oral beta-carotene supplementation." *Nutr Res* 19: 381-388.

Bell, J. G., J. McEvoy, et al. (1998). "Flesh Lipid and Carotenoid Composition of Scottish Farmed Atlantic Salmon (Salmo salar)." *J Agric Food Chem* 46(1): 119-127.

Bjerkeng, B. and G. M. Berge (2000). "Apparent digestibility coefficients and accumulation of astaxanthin E/Z isomers in Atlantic salmon (Salmo salar L.) and Atlantic halibut (Hippoglossus hippoglossus L.)." *Comp Biochem Physiol B Biochem Mol Biol* 127(3): 423-32.

Bracco, U. and R. Dececkbaum (1992). *Polyunsaturated fatty acids in human nutrition*. New York, N.Y., Raven Press.

Canizares-Villanueva, R. O., E. Rios-Leal, et al. (1998). "[Microbial sources of pigments]." *Rev Latinoam Microbiol* 40(1-2): 87-107.

Clark, R. M., L. Yao, et al. (2000). "A comparison of lycopene and astaxanthin absorption from corn oil and olive oil emulsions." *Lipids* 35(7): 803-6.

Deuel, H. (1951). *The lipids*. New York, N.Y., Interscience Publishers.

Fennema, O. (1996). *Food Chemistry*, Marcel Decker.

Furuita, H., T. Takeuchi, et al. (1998). "Effects of eicosapentaenoic and docosahexaenoic acids on growth, survival and brain development of larval Japanese flounder (*Paralichthys olivaceus*)." *Aquaculture* 161: 269-279.

Goto, S., K. Kogure, et al. (2001). "Efficient radical trapping at the surface and inside the phospholipid membrane is responsible for highly potent antiperoxidative activity of the carotenoid astaxanthin." *Biochim Biophys Acta* 1512(2): 251-8.

Hinostroza, G. C., A. Huberman,.et al. (1997). "Pigmentation of the rainbow trout (*Oncorhynchus mykiss*) with oil-extracted astaxanthin from the langostilla (*Pleuroncodes planipes*)." *Arch Latinoam Nutr* 47(3): 237-41.

Lockwood, S. F., S. O'Malley, et al. (2003). "Improved aqueous solubility of crystalline astaxanthin (3,3'-dihydroxy-beta, beta-carotene-4,4'-dione) by Captisol (sulfobutyl ether beta-cyclodextrin)." *J Pharm Sci* 92(4): 922-6.

Pane, L., L. Radin, et al. (1996). "The carotenoid pigments of a marine *Bacillus firmus* strain." *Boll Soc Ital Biol Sper* 72(11-12): 303-8.

Parajo, J. C., V. V. Santos, et al. (1998). "Production of carotenoids by *phaffia rhodozyma* growing on media made from hemicellulosic hydrolysates of eucalyptus globulus wood." *Biotechnol Bioeng* 59(4): 501-6.

Place, A. R and M. Harel (2002). Use of arachidonic acid for enhanced culturing of fish larvae and broodstock. US Pat. Publ. 20020110582 A1.

Shahidi, F., Metusalach, et al. (1998). "Carotenoid pigments in seafoods and aquaculture." *Crit Rev Food Sci Nutr* 38(1): 1-67.

Shibata, A., Y. Kiba, et al. (2001). "Molecular characteristics of astaxanthin and beta-carotene in the phospholipid monolayer and their distributions in the phospholipid bilayer." *Chem Phys Lipids* 113(1-2): 11-22.

Tsubokura, A., H. Yoneda, et al. (1999). "*Paracoccus carotinifaciens* sp. nov., a new aerobic gram-negative astaxanthin-producing bacterium." *Int J Syst Bacteriol* 49 Pt 1: 277-82.

Yeum, K. J. and R. M. Russell (2002). "Carotenoid bioavailability and bioconversion." *Annu Rev Nutr* 22: 483-504.

We claim:

1. A method of preparing a cold water fish feed composition which provides for an increased level of carotenoids in the fish consuming same, the method comprising (a) mixing one or more carotenoids and one or more phospholipids in an organic solvent to form a solution, wherein at least 20% of fatty acid residues in the phospholipids have 4 or more double bonds; and (b) thereafter combining the carotenoid(s) and phospholipid(s) with at least one other animal feed component;
   wherein the organic solvent is a polar solvent selected from the group consisting of chlorocarbons and lower alcohols, and wherein step (a) further comprises removing the polar solvent from the solution.

2. The method of claim 1, wherein the feed composition is a pelleted feed composition.

3. The method of claim 1, wherein the at least one other feed component is in pelleted form and wherein step (b) comprises coating the at least one other feed component.

4. The method of claim 3, wherein in step (b) the carotenoid(s) and phospholipid(s) are in a mixture with an oil and the coating is performed with the mixture.

5. The method of claim 1, wherein multiple carotenoids are used and the combined carotenoids make up at least 1%, by weight, of the composition.

6. The method of claim 1, wherein step (a) comprises vortex mixing, high shear mixing, sonication or molecular level mixing.

7. The method of claim 1, wherein the mixing time is in a range from about 5 minutes to several hours.

8. The method of claim 1, wherein the mixing temperature is in a range from ambient temperature to about 60° C.

9. The method of claim 1, wherein at least 40% of fatty acid residues in the phospholipid(s) are DHA residues.

10. The method of claim 1, wherein at least 20% of fatty acid residues in the phospholipid(s) are EPA residues.

* * * * *